United States Patent [19]

Kaiser et al.

[11] Patent Number: 5,919,440
[45] Date of Patent: *Jul. 6, 1999

[54] PERSONAL CARE COMPOSITIONS CONTAINING AN ODOR MASKING BASE

[75] Inventors: Carl-Eric Kaiser, Cincinnati; Charles Raymond Tremblay, Mason, both of Ohio

[73] Assignee: Procter & Gamble Company, Cincinnati, Ohio

[ * ] Notice: This patent is subject to a terminal disclaimer.

[21] Appl. No.: 08/851,433

[22] Filed: May 5, 1997

[51] Int. Cl.$^6$ ............................... A61K 7/48; A61K 7/46
[52] U.S. Cl. ....................... 424/76.4; 424/78.02; 424/401
[58] Field of Search .................................. 424/401, 76.4, 424/78.02

[56] References Cited

U.S. PATENT DOCUMENTS

| | | | |
|---|---|---|---|
| 3,679,754 | 7/1972 | Beereboom | 260/587 |
| 4,963,348 | 10/1990 | Bolich, Jr. et al. | 424/71 |
| 5,120,532 | 6/1992 | Wells et al. | 424/70 |
| 5,135,747 | 8/1992 | Faryniarz et al. | 424/401 |
| 5,190,915 | 3/1993 | Behan et al. | 512/2 |
| 5,378,731 | 1/1995 | Andrews et al. | 514/552 |
| 5,501,805 | 3/1996 | Behan et al. | 252/8.6 |
| 5,540,853 | 7/1996 | Trinh et al. | 510/101 |
| 5,543,157 | 8/1996 | Trinh et al. | 424/493 |
| 5,554,588 | 9/1996 | Behan et al. | 512/1 |
| 5,679,324 | 10/1997 | Lisboa et al. | 424/45 |
| 5,683,979 | 11/1997 | Schreck et al. | 512/13 |

FOREIGN PATENT DOCUMENTS

| | | |
|---|---|---|
| 730095 | 5/1955 | United Kingdom . |
| 995175 | 6/1965 | United Kingdom . |

*Primary Examiner*—Jyothsna Venkat
*Attorney, Agent, or Firm*—Joan B. Tucker; William J. Winter; Tara M. Rosnell

[57] ABSTRACT

Disclosed are personal care compositions comprising (a) from about 0.1% to about 99.85% by weight of a malodor-producing liquid carrier, malodor-producing polymer, or combination thereof, and (b) from about 0.005% to about 2.5% by weight of an odor masking base. The base comprises from about 15% to about 75% by weight of the base of an ionone perfume having a boiling point of more than about 250° C., from about 5% to about 65% by weight of the base of a musk having a boiling point of more than about 250° C., and from about 20% to about 80% by weight of the base of a highly volatile perfume having a boiling point of less than about 250° C. The odor masking base of the composition helps to mask the malodor of the malodor-producing polymer and/or malodor-producing liquid carrier.

24 Claims, No Drawings

PERSONAL CARE COMPOSITIONS CONTAINING AN ODOR MASKING BASE

FIELD OF THE INVENTION

The present invention relates to personal care compositions which contain a select combination of perfume materials which help to mask malodors associated with the use of malodor-producing polymers and/or malodor-producing liquid carriers in the compositions.

BACKGROUND OF THE INVENTION

Personal care products are commercially available in a variety of forms including antiperspirants, deodorants, hand and body lotions, shampoos, liquid and bar soaps, body washes, disposable diapers, and the like. Most of these products contain perfumes which help provide a pleasant fragrance during or after application of the product, or which otherwise help to hide or mask malodors associated with the use of such products.

Many personal care products are never commercialized because it is often too difficult to sufficiently hide or mask malodors associated with the use of such products. Especially problematic are malodors associated with the use of personal care products containing styling polymers, volatile liquid carriers, or combinations thereof. These malodors are even more problematic and difficult to hide or mask with most perfumes when higher concentrations of such malodor-producing polymers and/or malodor-producing liquid carriers are used in the personal care product. These higher concentrations are often necessary to provide improved product benefits such as skin and hair softness, hairstyle, mildness, increased deposition of active ingredients, fragrance longevity, and so forth.

Polymer or liquid carrier malodors, especially those in personal care products, can be made less offensive by using even higher concentrations of perfumes. Although the addition of such higher concentrations of perfumes can alter or reduce the overall offensive character of the polymer or liquid carrier malodors, it often results in an undesirably overbearing perfume odor that is especially offensive when associated with a personal care product. Even when the higher perfume concentrations adequately modify, hide or otherwise mask the polymer or liquid carrier malodors, these higher concentrations do not necessarily result in improved perfume substantivity or longevity, thus resulting in the recurrence of liquid carrier or polymer malodors after the higher perfume concentrations have initially volatilized and no longer have an impact on malodors.

It has now been found that a select combination of perfume materials as defined herein can be incorporated into personal care compositions to effectively reduce the intensity of or mask the malodors associated with the use of malodor-producing polymers, malodor-producing liquid carriers or combinations thereof. This select combination of perfume chemicals comprises a highly volatile perfume, an ionone, and musk.

It is therefore an object of the present invention to provide an odor masking material suitable for use in personal care or other compositions containing malodor-producing liquid carriers and/or malodor-producing styling polymers, wherein the odor masking material effectively reduces or masks the malodor associated with the use of such compositions. It is a further object of the present invention to provide such an odor masking material which contains a select combination of a highly volatile perfume, an ionone, and musk.

SUMMARY OF THE INVENTION

The present invention is directed to personal care compositions which comprise (a) from about 0.1% to about 99.85% by weight of a malodor-producing liquid carrier, malodor-producing polymer, or combination thereof, and (b) from about 0.005% to about 2.5% by weight of an odor masking base. The odor masking base comprises (by weight of the base) from about 15% to about 75% by weight of an ionone perfume having a boiling point of more than about 250° C., from about 5% to about 65% by weight of a musk having a boiling point of more than about 250° C., and from about 20% to about 80% by weight of a highly volatile perfume having a boiling point of less than about 250° C.

It has been found that the select combination of perfume chemicals in the odor masking base effectively helps to mask malodors associated with personal care compositions containing malodor-producing polymers and/or malodor-producing liquid carriers.

DETAILED DESCRIPTION OF THE INVENTION

The personal care compositions of the present invention comprise a malodorous liquid carrier and/or malodorous polymer and an odor masking base to mask or reduce the malodor associated with the use of such malodorous liquid carriers and/or malodorous polymers. The odor masking base is a select combination of ionone perfume, musk, and a highly volatile perfume.

The term "malodor" as used herein refers to any detectable odor associated with a volatile liquid carrier and/or a personal care polymer as recognized by people with normal olfactory acuity.

The term "odor masking base" as used herein refers to a select combination of perfume materials defined herein which are capable of masking or reducing both the odor and scent of malodorous liquid carriers and/or malodorous polymers formulated in personal care compositions.

The term "malodor-producing liquid carrier" as used herein refers to the smell, scent, odor, aroma, or fragrance of the volatile liquid carriers as defined herein.

The term "malodor-producing polymer" as used herein refers to the smell, scent, odor, aroma, or fragrance of the personal care polymers as defined herein.

The term "soluble" as used herein refers to any material that is sufficiently soluble in the liquid carrier of the personal care composition herein to form a substantially clear solution to the naked eye at a concentration of about 0.2%, preferably at about 0.5%, even more preferably at about 1.0%, by weight of the material in the liquid carrier at 25° C.

The term "insoluble" as used herein refers to any material that is not sufficiently soluble in the liquid carrier of the personal care composition herein to form a substantially clear solution to the naked eye at a concentration of about 0.2%, preferably at about 0.1%, by weight of the insoluble material at 25° C.

The personal care compositions of the present invention can comprise, consist of, or consist essentially of the elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include carriers or by-products that may be included in commercially available materials, unless otherwise specified.

POLYMER

The personal care composition of the present invention may comprise a malodor-producing polymer, preferably a malodor-producing hair styling polymer, which is otherwise suitable for application to human hair or skin. Concentrations of the malodor-producing polymer range from about 0.1% to about 99.85%, preferably from about 0.5% to about 75%, more preferably from about 0.5% to about 50%, and even more preferably from about 1% to about 25%, by weight of the personal care composition.

Malodor-producing polymers suitable for use in the personal care composition of the present invention include gums and resins which are primarily derived from natural sources; crosslinked nonionic polyacrylate polymers and crosslinked cationic polyacrylate polymers such as homopolymers, copolymers, terpolymers of quaternary ammonium or cationic amine-substituted monomer units; polysaccharide polymers such as those derived from cellulose and starch; protein polymers; carboxylic acid polymers such as crosslinked acrylic acid homopolymers or copolymers; substituted or unsubstituted, linear or branched polyacrylamide polymers; copolymers of alkyl vinyl ethers and maleic anhydride; polyvinyl (N-pyrrolidones); silicone polymer materials (excluding the volatile silicone derivatives useful as a malodor-producing liquid carrier described hereinbelow) such as polydimethylsiloxane gums, silicone elastomers, siloxane gums, resin reinforced siloxanes, and crosslinked siloxane polymers; silicone copolymers useful as hair styling polymers; and mixtures thereof.

Nonlimiting examples of malodor-producing polymers suitable for use in the composition are disclosed in the CTFA *Cosmetic Ingredient Dictionary*, 3rd edition, edited by Estrin, Crosley, and Haynes (The Cosmetic, Toiletry, and Fragrance Association, Inc., Washington, D.C. (1982)); EP 228,868, to Farrar et al., published Jul. 15, 1987; EP 412,704, published Feb. 7, 1991; EP 412,707, published Feb. 13, 1991; U.S. Ser. No. 07/758,319, Bolich et al., filed Aug. 27, 1991; U.S. Ser. No. 07/758,320, Torgerson et al., filed Aug. 27, 1991; U.S. Pat. No. 4,061,602, to Oberstar et al., issued Dec. 6, 1977; U.S. Pat. No. 4,196,190, to Gehman et al., issued Apr. 1,1980; U.S. Pat. No. 4,221,688, to Johnson et al., issued Sep. 9, 1980; U.S. Pat. No. 4,234,464, to Morshauser, issued Nov. 18, 1980; U.S. Pat. No. 4,272,511, to Papantoniou et al., issued Jun. 9, 1981; U.S. Pat. No. 4,472,297, to Bolich et al., issued Sep. 18, 1984; U.S. Pat. No. 4,491,539, to Hoskins et al., issued Jan. 1, 1985; U.S. Pat. No. 4,509,949, to Huang et al., issued Apr. 5, 1985; U.S. Pat. No. 4,540,507, to Grollier, issued Sep. 10, 1985; U.S. Pat. No. 4,599,379, to Flesher et al., issued Jul. 8, 1986; U.S. Pat. No. 4,628,078, to Glover et al., issued Dec. 9, 1986; U.S. Pat. No. 4,673,525, to Small et al., issued Jun. 16, 1987; U.S. Pat. No. 4,693,935, to Mazurek, issued Sep. 15, 1987; U.S. Pat. No. 4,728,571, to Clemens et al., issued Mar. 1, 1988; U.S. Pat. No. 4,835,206, to Farrar et al., issued May 30, 1989; U.S. Pat. No. 4,849,484, to Heard, issued Jul. 18, 1989; U.S. Pat. No. 4,902,499, to Bolich et al., issued Feb. 20, 1990; U.S. Pat. No. 4,906,459, to Bolich et al., issued Mar. 6, 1990; U.S. Pat. No. 5,073,614, to Shih et al., issued Dec. 17, 1991; U.S. Pat. No. 5,087,445, to Haffey et al., issued Feb. 11, 1992; U.S. Pat. No. 5,100,660, to Hawe et al., issued Mar. 31, 1992; U.S. Pat. No. 5,104,642 to Wells. et al., issued Apr. 14, 1992; U.S. Pat. No. 5,104,646, to Bolich et al., issued Apr. 14, 1992; U.S. Pat. No. 5,106,609, to Bolich et al., issued Apr. 21, 1992; U.S. Pat. No. 5,120, 531, to Wells et al., issued Jun. 9, 1992; U.S. Pat. No. 5,120,532, to Wells et al., issued Jun. 9, 1992; U.S. Pat. No. 5,139,770, to Shih et al., issued August 18, 1992; and U.S. Pat. No. 5,494,533, to Woodin Jr. et al., issued Feb. 27, 1996, which descriptions are incorporated herein by reference.

Preferred malodor-producing polymers are those film forming polymers especially suited for use in hair styling compositions such as hair sprays, styling shampoos, styling mousses, and the like, and which have a noticeable malodor when not used in combination with the odor masking base described hereinafter. Most preferred are hair styling polymers selected from the group consisting of copolymers of 1-vinyl-2-pyrrolidone and 1-vinyl-3-methylimidazolium salt (e.g., chloride salt) (referred to in the industry as Polyquaternium-16), such as those commercially available from BASF Wyandotte Corp. (Parsippany, N.J., USA) under LUVIQUAT tradename (e.g., LUVIQUAT FC 370 and LUVIQUAT FC 550); t-butyl acrylate/2-ethylhexyl acrylate copolymers having a weight/weight ratio of monomers of about 95/5, about 90/10, about 80/20, about 70/30, about 60/40, and about 50/50; t-butyl acrylate/2-ethylhexyl methacrylate copolymers having a weight/weight ratio of monomers of about 95/5, about 90/10, about 80/20, about 70/30, about 60/40, and about 50/50; t- butyl methacrylate/2-ethylhexyl acrylate copolymers having a weight/weight ratio of monomers of about 95/5, about 90/10, about 80/20, about 70/30, about 60/40, and about 50/50; t-butyl methacrylate/ 2-ethylhexyl methacrylate copolymers having a weight/ weight ratio of monomers of about 95/5, about 90/10, about 80/20, about 70/30, about 60/40, and about 50/50; t-butyl ethacrylate/2-ethylhexyl methacrylate copolymers having a weight/weight ratio of monomers of about 95/5, about 90/10, about 80/20, about 70/30, about 60/40, and about 50/50; vinyl pyrrolidone/vinyl acetate copolymers having a weight/weight ratio of monomers of about 10/90, and about 5/95; and mixtures thereof.

Liquid Carrier

The personal care composition of the present invention may comprise a malodor-producing liquid carrier suitable for application to human hair or skin, and which is preferably suitable for dissolving or dispersing film forming polymers in a hair styling composition, especially when the film forming polymer is a malodor-producing polymer as described hereinbefore. The liquid carrier is included in the personal care composition at concentrations of from about 0.10% to about 99.85%, preferably from about 0.5% to about 75%, more preferably from about 1% to about 50%, even more preferably from about 1% to about 25%, by weight of the composition.

The personal care composition preferably comprises a combination of a liquid carrier and a film forming polymer, wherein the combination is associated with a malodor when used in a personal care composition. The malodor associated with such a combination may or may not be easily attributable solely to the liquid carrier or the film forming polymer, but rather may be most easily attributable to the combination.

The liquid carrier for use in the personal care composition of the present invention is preferably a malodor-producing liquid carrier, typically a volatile organic solvent which produces malodors when used in personal care applications. In this context, the term "volatile" refers to liquid carriers that have a boiling point of less than about 300° C., preferably less than about 260° C., more preferably less than about 200° C. (under 1 atmosphere of pressure).

Suitable volatile organic solvents include many liquid carriers which are well known in the chemical arts, for example hydrocarbons, ethers, esters, amines, alkyl alcohols, volatile silicones derivatives, and combinations thereof. Nonlimiting examples of volatile organic solvents for use in the personal care composition of the present invention include linear or branched, saturated or unsaturated hydrocarbon solvents having from about 8 to about 18 carbon atoms; di($C_5$–$C_7$) alkyl ethers and diethers such as isoamyl ether, dipentyl ether, and dihexyl ether; $C_5$–$C_{12}$ alkyl esters such as ethyl butyrate, diethyl malonate, diethyl phthalate, diethyl succinate, dimethyl succinate, isopropyl butyrate; $C_1$–$C_4$ alcohols such as ethanol, butyl alcohol, amyl alcohol, benzyl alcohol, phenyl propanol, and isopropanol; and volatile silicone derivatives such as cyclic or linear polydialkylsiloxane, linear siloxy compounds, or silane compounds.

Odor Masking Base

The personal care compositions of the present invention comprise an odor masking base which comprises a select combination of a highly volatile perfume, ionone perfume, and musk.

Concentrations of the odor masking base preferably range from about 0.005% to about 3%, more preferably from about 0.006% to about 2.5%, even more preferably from about 0.0075% to about 1%, by weight of the personal care composition.

The ionones, musks and highly volatile perfumes of the odor masking base are characterized in part by their respective boiling point ranges. The ionone perfumes and musks must have a boiling point under I atmosphere of pressure of more than about 250° C., whereas the highly volatile perfumes must have a boiling point under I atmosphere of pressure of less than about 250° C.

The boiling point of many perfume materials are disclosed in, e.g., "Perfume and Flavor Chemicals (Aroma Chemicals)," S. Arctander, published by the author, 1969, incorporated herein by reference. Other boiling point values can be obtained from different chemistry handbooks and databases, such as the Beilstein Handbook, Lange's Handbook of Chemistry, and the CRC Handbook of Chemistry and Physics. When a boiling point is given only at a different pressure, usually lower pressure than the normal pressure of one atmosphere, the boiling point at normal or ambient pressure can be approximately estimated by using boiling point-pressure nomographs, such as those given in "The Chemist's Companion," A. J. Gordon and R. A. Ford, John Wiley & Sons Publishers, 1972, pp. 30–36. When applicable, the boiling point values can also be calculated by computer programs, based on molecular structural data, such as those described in "Computer-Assisted Prediction of Normal Boiling Points of Pyrans and Pyrroles," D. T. Stanton et al, J. Chem. Inf. Comput. Sci., 32 (1992), pp. 306–316, "Computer-Assisted Prediction of Normal Boiling Points of Furans, Tetrahydrofurans, and Thiophenes," D. T. Stanton et al, J. Chem. Inf. Comput. Sci., 31 (1992), pp. 301–310, and references cited therein, and "Predicting Physical Properties from Molecular Structure," R. Murugan et al, Chemtech, June 1994, pp. 17–23. All the above publications are incorporated herein by reference.

Each of the ionone perfumes, highly volatile perfumes, and musk components of the odor masking base are described in detail hereinafter. The present invention is also directed to the odor masking base, whether or not it is incorporated into the personal care composition described herein. Such an odor masking base comprises each of the ionone perfumes, highly volatile perfumes, and musk components as described herein. Such an embodiment can be used as an odor masking base or perfume in a variety of applications, including as an odor masking base associated with products or compositions other than personal care compositions.

Highly Volatile Perfume

The highly volatile perfume of the odor masking base comprises perfume materials which compete with the malodorous liquid carrier and/or malodorous polymer molecules to bind to the nasal receptor sites. These highly volatile perfumes are the first odors recognized and identified by the brain, and help inhibit or mask the olfactory recognition of the malodorous liquid carrier and/or malodorous polymer. Concentrations of the highly volatile perfume range from about 15% to about 85%, preferably from about 20% to about 80%, more preferably from about 35% to about 75%, even more preferably from about 45% to about 65%, by weight of the odor masking base.

The highly volatile perfumes are more volatile than the ionone and musk components of the odor masking base, and have a boiling point of less than about 250° C., preferably less than about 230° C., more preferably less than about 220° C. under 1 atmosphere of pressure. These highly volatile perfumes are classified as either aldehydes having from about 2 to about 15 carbon atoms, esters having from about 3 to about 15 carbon atoms, alcohols having from about 4 to about 12 carbon atoms, ethers having from about 4 to about 13 carbon atoms, ketones having from about 3 to about 12 carbon atoms, or combinations thereof.

Nonlimiting examples of suitable aldehydes include n-decyl aldehyde, 10-undecen-1-al, dodecanal, 3,7-dimethyl-7-hydroxyoctan- 1-al, 2,4-dimethyl-3-cyclohexene carboxaldehyde, benzaldehyde, anisic aldehyde, and mixtures thereof.

Nonlimiting examples of suitable esters include ethyl acetate, cis-3-hexenyl acetate, 2,6-dimethyl-2,6-octadien-8-yl acetate, benzyl acetate, 1,1-dimethyl-2-phenyl acetate, 2-pentyloxy allyl ester, allyl hexanoate, methyl-2-aminobenzoate, and mixtures thereof.

Nonlimiting examples of suitable alcohols include n-octyl alcohol, beta-gamma-hexenol, 2-trans-6-cis-nonadien-1-ol, 3,7-dimethyl-trans-2,6-octadien-l-ol, 3,7-dimethyl-6-octen-1-ol, 3,7-dimethyl- 1,6-octadien-3-ol, 2,6-dimethyl-7-octen-2-ol, 2-phenylethyl alcohol, 2-cis-3,7-dimethyl-2,6-octadien-1-ol, 1-methyl-4-iso-propyl-1-cyclohexen-8-ol, and mixtures thereof.

Nonlimiting examples of suitable ethers include amyl cresol oxide, 4-ethoxy-1-methyl-benzol, 4-methoxy-1-methyl benzene, methyl phenylethyl ether, and mixtures thereof.

Nonlimiting examples of suitable ketones include dimethyl acetophenone, ethyl-n-amyl ketone, 2-heptanone, 2-octanone, 3-methyl-2-(cis-2-penten- 1-yl)-2-cyclopenten-1-one, 1-1-methyl-4-iso-propenyl-6-cyclohexen-2-one, para-tertiary-amyl cyclohexanone, and mixtures thereof.

Preferred highly volatile perfumes include 2-pentyloxy allyl ester sold under the tradename Allyl Amyl Glycolate (available from International Flavors and Fragrances, Inc. located in New York, N.Y., U.S.A.); benzaldehyde sold under the tradename Amandol (available from Rhone-Poulenc, Inc located in Princeton, N.J., U.S.A.); cis-3-hexenyl acetate sold under the tradename Verdural extra (available from International Flavors and Fragrances, Inc. located in New York, N.Y., U.S.A.); 2,6-dimethyl-7-octen-2-ol sold under the tradename Dihydromyrcenol (available from International Flavors and Fragrances, Inc. located in New York, N.Y., U.S.A.); para-tertiary-amyl cyclohexanone sold under the tradename Orivone (available from International Flavors and Fragrances, Inc. located in New York, N.Y., U.S.A.); n-decyl aldehyde sold under the tradename Decyl Aldehyde (available from Aceto, Corp. located in Lake Success, N.Y., U.S.A.); and mixtures thereof.

Nonlimiting examples of suitable highly volatile perfumes and their respective boiling point values under 1 atmosphere of pressure include the following:

| Perfume Material | Boiling Point (° C.) |
| --- | --- |
| 3,7-dimethyl-1,6-octadien-3-ol | 198 |
| 3,7-dimethyl-7-hydroxyoctan-1-al | 241 |
| n-decyl aldehyde | 215 |
| benzaldehyde | 179 |
| anisic aldehyde | 248 |
| benzyl acetate | 215 |
| allyl hexanoate | 185 |
| cis-3-hexenyl acetate | 87 |
| methyl-2-aminobenzoate | 237 |
| 2-pentyloxy allyl ester | Flash Point > 100 |
| 2-cis-3,7-dimethyl-2,6-octadien-1-ol | 227 |
| 3,7-dimethyl-trans-2,6-octadien-1-ol | 230 |
| 3,7-dimethyl-6-octen-1-ol | 225 |
| 2,6-dimethyl-7-octen-2-ol | 208 |
| 2-phenylethyl alcohol | 220 |
| 1-methyl-4-iso-propyl-1-cyclohexen-8-ol | 219 |
| 1-1-methyl-4-iso-propenyl-6-cyclohexen-2-one | 231 |
| para-tertiary-amyl cyclohexanone | 211 |

Ionone Perfume

The odor masking base comprises an ionone perfume at concentrations ranging from about 15% to about 80%, preferably from about 16% to about 60%, more preferably from about 16% to about 40%, by weight of the odor masking base. These ionone perfumes are a well known class of perfumes chemicals derived from natural oils or manufactured synthetically, which are typically colorless or pale yellow liquids exhibiting woody violet-like odors.

The ionone perfume for use in the odor masking base must have a boiling point under 1 atmosphere of pressure of more than about 250° C., preferably more than about 255° C., even more preferably more than about 260° C., wherein the ionone perfume is preferably selected from methyl ionones, alpha ionones, beta ionones, gamma ionones, or combinations thereof.

Nonlimiting examples of suitable ionones include 1-(2,6,6-Trimethyl-2-cyclohexene-1-yl)-1,6-heptadien-3-one, 2-Allyl-para-menthene-(4(8))-ono-3, Pseudo-allyl-alpha-ionone, alpha-Citrylidene cyclopentanone, 5-(2,6,6-Trimethyl-2-cyclohexen- 1-yl)-4-methyl-4-penten-3-one, 6-(2,6,6-Trimethyl-2-cyclohexen- 1-yl)- 1-methyl-5-hexen-4-one, 2,6,6-Trimethyl cyclohexyl-1-butenone-3, Dihydro-alpha-ionone, 4-(2,6,6-Trimethylcyclohexen-1-yl)-butan-2-one, 4-(2-Methylene-6,6-dimethylcyclohexyl)-butan-2-one, 1-(2,5,6,6-Tetramethyl-2-cyclohexenyl)-butan-3-one, Dihydro-beta-irone, Dihydro-gamma-irone, 5-(2,6,6-Trimethyl-2-cyclohexenyl)-pentan-3-one, Dihydro-iso-methyl-beta-ionone, 6-(2,6,6-Trimethyl-2-cyclohexen-1-yl)-5-hexen-4-one, alpha-Ethyl-2,2,6-trimethyl cyclohexane butyric aldehyde, 4-Methyl-6-(1,1,3-trimethyl-2'-cyclohexen-2'-yl)-3,5-hexadien-2-one, 6,10-Dimethyl undecan-2-one, 6-(2,6,6-Trimethyl-1-cyclohexen- 1-yl)-1-methyl-2,5-hexadien-4-one, 6-(2,6,6-Trimethyl-2-cyclohexen- 1-yl)- 1-methyl-2,5-hexadien-4-one, 4-(2,2,6-Trimethyl-2-cyclohexen-1-yl)-3-buten-2-one, 4-(2,6,6-Trimethyl-1-cyclohexen- 1-yl)-3-buten-2-one, 4-(2-Methylene-6,6-dimethylcyclohexyl)-3-buten-2-one, Epoxy-2,3-beta-ionone, Ethyl-2,3-epoxy-3-methyl-5-(2,6,6-trimethyl-2-cyclohexenyl)-4-pentenoate, alpha-ionone methylanthranilate, Methyl-2,3-epoxy-3-methyl-5-(2,6,6-trimethyl-2-cyclohexenyl)-4-pentenoate, 4-(2,5,6,6-Tetramethyl-2-cyclohexen-1-yl)-3-buten-2-one, 6-Methyl-beta-ionone, 6-Methyl-gamma-ionone, 4-(2,6,6-Trimethyl-2-cyclohexenyl)-2,3-dimethyl-2-buten- 1-al, 4-(2,6,6-Trimethyl-2-cyclohexen-1-yl)-3-methyl-3-buten-2-one, 5-(2,6,6-Trimethyl-2-cyclohexen-1-yl)-4-penten-3-one, 5-(2,6,6-Trimethyl-1-cyclohexen-1-yl)-4-penten-3-one, 4-(2,6,6-Trimethyl-3-cyclohexen-1-yl)-3-methyl-3-buten-2-one, 5-(2-Methylene-6,6-dimethylcyclohexyl)-4-penten-3-one, 4-(2-Methylene-6,6-dimethylcyclohexyl)-3-methyl-3-buten-2-one, 4-(2,3,6,6-Tetramethyl-2-cyclohexen-1-yl)-3-buten-2-one, 4-(2,4,6,6-Tetramethyl-2-cyclohexen- 1-yl)-3-buten-2-one, 4-(2,4,6,6-Tetramethyl-1-cyclohexen-1-yl)-3-buten-2-one, 5-Methyl-1-(3-methyl-3-cyclohexenyl)- 1,3-hexanedione, 2-Methyl-4-(2,6,6-trimethyl-2-cyclohexenyl)-3-buten- 1-al, 3-Methyl-4-(2,4,6-trimethyl-3-cyclohexenyl)-3-buten-2-one, 4-(2-Methyl-5-iso-propenyl-1-cyclopenten-1-yl)-2-butanone, 4-(2,6,6-Trimethyl-7-cycloheptenyl)-3-buten-2-one, 4-(2,6,6-Trimethyl-4-cyclohexenyl)-3-buten-2-one, 2,6-Dimethylundeca-2,6,8-trien-10-one, 2,6,12-Trimethyl-trideca-2,6,8-trien-10-one, 2,6-Dimethyldodeca-2,6,8-trien-10-one, 2,6,9-Trirethylundeca-2,6,8-trien-10-one, 4-(2,6,6-Trimethyl-2-cyclohexen-1-yl)-3-methyl-3-buten-2-one, 4-(2,4,6-Trimethyl-3-cyclohexen-1-yl)-3-buten-2-one, 5-(2-Methylene-6,6-dimethylcyclohexyl)-4-penten-3-one, and mixtures thereof.

Preferred ionones include 4-(2,6,6-Trimethyl-3-cyclohexen-1-yl)-3-methyl-3-buten-2-one sold under the tradename Isoraldeine (available from Givaudan Roure, Corp. located in Teaneck, N.J., U.S.A.); 5-(2-Methylene-6,6-dimethylcyclohexyl)-4-penten-3-one sold under the tradename gamma-Methyl Ionone (available from Givaudan Roure, Corp. located in Teaneck, N.J., U.S.A.); 4-(2,2,6-Trimethyl-2-cyclohexen-1-yl)-3-buten-2-one sold under the tradename alpha-Ionone (available from International Flavors and Fragrances, Inc. located in New York, N.Y., U.S.A); 4-(2,6,6-Trimethyl-1-cyclohexen-1-yl)-3 -buten-2-one sold under the tradename beta-Ionone (available from International Flavors and Fragrances, Inc. located in New York, N.Y., U.S.A); 4-(2,6,6-Trimethyl-2-cyclohexen-1-yl)-3-methyl-3-buten-2-one sold under the tradename Methyl Ionone (available from Bush Boake Allen, Inc. located in Montvale, N.J., U.S.A.); and mixtures thereof.

Ionones may be incorporated into the odor masking base as one or more individual perfume chemicals or as a specialty perfume containing a combination of perfume chemicals including ionone perfume chemicals. Nonlimiting examples of ionone specialty perfumes include Alvanone Extra available from International Flavors and Fragrances, Inc. located in New York, N.Y., U.S.A., Irisia Base available from Firmenich, Inc located in Princeton, N.J., U.S.A., Irival available from International Flavors and Fragrances, Inc. located in New York, N.Y., U.S.A., Iritone available from International Flavors and Fragrances, Inc. located in New York, N.Y., U.S.A., and mixtures thereof.

The musk and highly volatile perfumes for use in the odor masking base can also be incorporated into the base as one or more individual perfume chemicals, or as a specialty perfume containing a combination of perfume chemicals. A nonlimiting example of a preferred highly volatile specialty perfume include Cassis Base 345-B available from Firmenich, Inc. located in Princeton, N.J., U.S.A..

Nonlimiting examples of suitable ionone perfumes and their respective boiling point values under 1 atmosphere of pressure include the following:

| Perfume Material | Boiling Point (° C.) |
|---|---|
| 2,6-Dimethylundeca-2,6,8-trien-10-one | 266 |
| Dihydro-alpha-ionone | 257 |
| 4-(2,6,6-Trimethylcyclohexen-1-yl)-butan-2-one | 253 |
| 4-(2,2,6-Trimethyl-2-cyclohexen-1-yl)-3-buten-2-one | 264 |
| 4-(2,6,6-Trimethyl-1-cyclohexen-1-yl)-3-buten-2-one | 266 |
| 4-(2,5,6,6-Tetramethyl-2-cyclohexen-1-yl)-3-buten-2-one | 286 |
| 5-(2,6,6-Trimethyl-1-cyclohexen-1-yl)-4-penten-3-one | 270 |
| 4-(2,6,6-Trimethyl-2-cyclohexen-1-yl)-3-methyl-3-buten-2-one | 275 |
| 4-(2,4,6-Trimethyl-3-cyclohexen-1-yl)-3-buten-2-one | 276 |
| 5-(2-Methylene-6,6-dimethylcyclohexyl)-4-penten-3-one | 270 |

Musk

The odor masking base comprises a musk component at concentrations of from about 5% to about 70%, preferably from about 15% to about 50%, more preferably from about 20% to about 35%, by weight of the odor masking base. Musk is a well known class of perfumes chemicals that is typically in the form of a colorless or light yellow material having a distinctive, musk-like odor.

The musk component for use in the odor masking base must have a boiling point under 1 atmosphere of pressure of more than about 250° C., preferably more than about 255° C., even more preferably more than about 260° C., wherein the musk component is preferably a polycyclic musk, macrocyclic musk, nitrocyclic musk, or combination thereof, each preferred musk component having more than about 12 carbon atoms, preferably more than about 13 carbon atoms, more preferably more than about 15 carbon atoms.

Suitable polycyclic musks include 5-Acetyl-1,1,2,3,3,6-hexamethylindan, 4-Acetyl-1,1-dimethyl-6-tertiary-butylindan, 7-Acetyl-1,1,3,4,4,6-hexamethyl-1,2,3,4-tetrahydronaphthalene, 1,1,4,4-Tetramethyl-6-ethyl-7-acetyl-1,2,3,4-tetrahydronaphthalene, 1,3,4,6,7,8-Hexahydro-4,6,6,7,8,8-hexamethyl-cyclopenta-gamma-2-benzopyran, and mixtures thereof.

Suitable macrocyclic musks include cyclopentadecanolide, cyclopentadecanolone, cyclopentadecanone, 3-Methyl-1-cyclopentadecanone, cycloheptadecen-9-one-1, cycloheptadecanone, cyclohexadecen-7-olide, cyclohexadecen-9-olide, cyclohexadecanolide, ethylene tridecane dioate, 10-oxahexadecanolide, 11-oxahexadecanolide, 12-oxahexadecanolide, and mixtures thereof.

Suitable nitrocyclic musks include 1,1,3,3,5-Pentamethyl-4,6-dinitroindan, 2,6-Dinitro-3-methoxy-1-methyl-4-tertiary-butylbenzene, 2,6-Dimethyl-3,5-dinitro-4-tertiary-butyl-acetophenone, 2,6-Dinitro-3,4,5-trimethyl-tertiary-butyl-benzene, 2,4,6-Triinitro-1,3-dimethyl-5-tertiary-butylbenzene, and mixtures thereof.

Preferred musks include 1,3,4,6,7,8-Hexahydro-4,6,6,7,8,8-hexamethyl-cyclopenta-gamma-2-benzopyran sold under the tradename Galaxolide (available from International Flavors and Fragrances, Inc. located in New York, N.Y., U.S.A.); cyclopentadecanolide sold under the tradename Exaltolide (available from Firmenich, Inc. located in Princeton, N.J., U.S.A.); ethylene tridecane dioate sold under the tradename Ethylene Brassylate (available from Fragrance Resource, Inc. located in Keyport, N.J., U.S.A.); 7-Acetyl-1,1,3,4,4,6-hexamethyl-1,2,3,4-tetrahydronaphthalene sold under the tradename Tonalid (available from Givaudan Roure, Corp. located in Teaneck, N.J., U.S.A.); and mixtures thereof.

Nonlimiting examples of suitable musks and their respective boiling point values under 1 atmosphere of pressure include the following:

| Perfume Material | Boiling Point (° C.) |
|---|---|
| 7-Acetyl-1,1,3,4,4,6-hexamethyl-1,2,3,4-tetrahydronaphthalene | 354 |
| ethylene tridecane dioate | 332 |
| 5-Acetyl-1,1,2,3,3,6-hexamethylindan | +300 |
| 1,3,4,6,7,8-Hexahydro-4,6,6,7,8,8-hexamethyl-cyclopenta-gamma-2-benzopyran (50% IPM) | +250 |
| cyclohexadecen-7-olide | 300 |
| cyclopentadecanolide | 280 |
| cyclohexadecanolide | 294 |
| 2,6-Dinitro-3,4,5-trimethyl-tertiary-butyl-benzene | +250 |

Optional Components

The personal care compositions of the present invention may further comprise one or more optional components known or otherwise effective for use in personal care products, provided that the optional components are physically and chemically compatible with the essential components described herein, or do not otherwise unduly impair product stability, aesthetics or performance. Individual concentrations of such optional components may range from about 0.001% to about 40% by weight of the personal care compositions.

Nonlimiting examples of optional components for use in the personal care composition include water or other aqueous solubilizing agents, anti-dandruff agents, hair conditioning agents such as hydrocarbon oils, fatty esters, silicones (preferably silicone hair conditioning agents), dyes, pearlescent aids, foam boosters, additional surfactants or nonionic cosurfactants, pediculocides, pH adjusting agents, preservatives, proteins, skin active agents, sunscreens, vitamins, skin bleaching agents, skin treating agents, skin healing agents, and viscosity adjusting agents.

Optional Perfume Oil

The personal care compositions of the present invention may further comprise additional perfume chemicals or oils other than those described herein. These optional perfume chemicals or oils are used in addition to and in combination with the odor masking base, to provide the composition with the desired fragrance. Concentrations of the optional perfume chemicals or oils preferably range from about 0.05% to about 5%, more preferably from about 0.06% to about 4.75%, even more preferably from about 0.075% to about 3%, by weight of the composition.

Optional perfume chemicals or oils suitable for use in the personal care composition can be any perfume material, or a combination of perfume materials, other than those described hereinbefore and which provides the composition with the desired fragrance. These optional perfume chemicals or oils provide the composition with the desired fragrance, which is substantially unaffected by the malodor of the malodor-producing polymer and/or malodor-producing liquid carrier which is now reduced or masked by the odor masking base.

Preferably the optional perfume oils are used in combination with the odor masking base at a weight ratio of optional perfume oil to odor masking base of from about 50:50 to about 95:5, more preferably from about 55:45 to about 90:10, even more preferably from about 60:40 to about 85:15, most preferably from about 70:30 to about 80:20.

Nonlimiting examples of optional perfume chemicals or oils which are useful in the personal care composition herein are described in *Perfumery and Flavoring Synthetics,* 3rd Revised Edition, Paul Z. Bedoukian, 1986, *Perfume and Flavor Chemicals,* Volumes I and II, Steffen Arctander, 1969, which descriptions are incorporated herein by reference.

Optional Humectants, Moisturizers, and Skin Conditioners

The personal care compositions of the present invention may further comprise one or more humectant, moisturizing, or skin conditioning materials. A variety of these materials can be employed and each can be present at concentrations of from about 0.1% to about 20%, more preferably from about 1% to about 10%, and most preferably from about 2% to about 5%, by weight of the composition. These materials include guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Also useful herein are the propoxylated glycerols described in U.S. Pat. No. 4,976,953, to Orr et al., issued Dec. 11, 1990, which is incorporated by reference herein in its entirety.

Also useful are various $C_1$–$C_{30}$ monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. The ester materials are further described in, U.S. Pat. No. 2,831,854, U.S. Pat. No. 4,005,196, to Jandacek, issued Jan.25, 1977; U.S. Pat. No. 4,005,195, to Jandacek, issued Jan. 25, 1977; U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Method of Masking

The present invention is also directed to methods of masking or reducing the malodor of personal care or other compositions containing malodor-producing liquid carriers and/or malodor-producing polymers. Such methods comprise the steps of (a) preparing an odor masking base by combining the following components: (i) from about 20% to about 80% by weight of the base of a highly volatile perfume, (ii) from about 15% to about 75% by weight of the base of an ionone perfume, and (iii) from about 5% to about 65% by weight of the base of a musk component; and (b) mixing the odor masking base of step (a) with the malodor-producing polymer, malodor-producing liquid carrier, or combination thereof, wherein the composition comprises from about 0.005% to about 2.5% by weight of the odor masking base, and from about 0.1% to about 99.85% by weight of the malodor-producing polymer, malodor-producing liquid carrier, or combination thereof. The methods preferably comprise the preferred composition limitations described hereinbefore.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. The exemplified embodiments of the personal care composition of the present invention provide masking or reduction of malodorous liquid carriers and/or malodorous polymers contained in the composition. Ingredients are herein identified by chemical, trade, of CTFA name.

The personal care compositions illustrated in Examples IX–XXII are prepared by conventional formulation and mixing techniques, an example of which is set forth hereinbelow. All exemplified amounts are listed as weight percents and exclude minor materials such as diluents, filler, and so forth, unless otherwise specified.

In the perfume art, some materials having no odor or very faint odor are used as diluents or extenders. Non-limiting examples of these materials are dipropylene glycol, diethyl phthalate, triethyl citrate, isopropyl myristate, and benzyl benzoate. These materials are used for, e.g., diluting and stabilizing some other perfume materials. These materials are not counted in the formulation of the personal care compositions of the present invention.

Preparation

The personal care compositions of the present invention may be prepared by composing an odor masking base as described in Examples I–VIII. The odor masking base and a perfume oil are then mixed with other ingredients of the composition using conventional formulation and mixing techniques. Odor masking base compositions, as well as perfume blends of the odor masking base and perfume oil, are exemplified in the following examples. The perfume blends can be a combination of odor masking base/perfume oil which is combined with other ingredients of the personal care composition.

Odor Masking Base

| Fragrance Material | I WT % | II WT % | III WT % | IV WT % |
|---|---|---|---|---|
| Allyl Amyl Glycolate[1] | 0.30 | 0.50 | 0.60 | 0.60 |
| Benzaldehyde[2] | 0.20 | 0.40 | 0.40 | 0.40 |
| Cassis 345-B[3] | 1.50 | 2.0 | 3.0 | 3.0 |
| cis-3-Hexenyl acetate[4] | 1.0 | 0.75 | 1.0 | 0.75 |
| Dihydromercenol[5] | 64.50 | 61.85 | 57.0 | 46.65 |
| Orivone[6] | — | 2.0 | 1.0 | 1.0 |
| Irisia Base[7] | 12.0 | — | 10.0 | 8.0 |
| Alvanone Extra[8] | — | — | 2.0 | — |
| n-Decyl aldehyde[9] | 0.50 | 0.50 | 0.50 | 0.60 |
| Tonalid[10] | — | — | — | 10.0 |
| Galaxolide 50 DEP[11] | 15.0 | 18.0 | 21.50 | 20.0 |
| Methyl Ionone[14] | — | 7.0 | — | 1.0 |
| gamma-Methyl Ionone[15] | 5.0 | 7.0 | 3.0 | 8.0 |

| Fragrance Material | V WT % | VI WT % | VII WT % | VIII WT % |
|---|---|---|---|---|
| Allyl Amyl Glycolate[1] | 0.75 | 0.40 | 2.0 | 2.0 |
| Benzaldehyde[2] | 0.60 | 0.40 | 1.0 | 1.5 |
| Cassis 345-B[3] | 3.0 | 2.50 | 3.0 | 3.0 |
| cis-3-Hexenyl acetate[4] | 1.0 | 0.75 | 2.0 | 1.5 |
| Dihydromercenol[5] | 58.65 | 61.25 | 36.0 | 11.0 |
| Orivone[6] | 2.0 | 1.0 | — | — |
| Irisia Base[7] | 5.0 | 10.0 | 5.0 | 5.0 |
| Alvanone Extra[8] | 2.0 | 1.0 | — | 1.0 |
| n-Decyl aldehyde[9] | 1.0 | 0.70 | 1.0 | 1.0 |
| Tonalid[10] | 5.0 | — | — | 5.0 |
| Galaxolide 50 DEP[11] | 15.0 | 20.0 | 20.0 | 20.0 |
| alpha-Ionone[12] | — | — | 10.0 | 20.0 |
| beta-Ionone[13] | — | — | 10.0 | 10.0 |
| Methyl Ionone[14] | — | — | — | 5.0 |
| gamma-Methyl Ionone[15] | 6.0 | 2.0 | 10.0 | 15.0 |

[1]available from International Flavors and Fragrances, Inc.
[2]available from Rhone-Poulene, Inc. under the tradename Amandol
[3]specialty perfume material available from Firmenich, Inc.
[4]available from International Flavors and Fragrances, Inc. under the tradename Verdural extra
[5]available from International Flavors and Fragrances, Inc.
[6]available from International Flavors and Fragrances, Inc.
[7]specialty perfume material available from Firmenich, Inc.
[8]specialty perfume material available from International Flavor and Fragrances, Inc.
[9]available from Aceto, Corp.
[10]available from Givaudan Roure, Corp.
[11]available from International Flavors and Fragrances, Inc.
[12]available from International Flavors and Fragrances, Inc.
[13]available from International Flavors and Fragrances, Inc.
[14]available from International Flavors and Fragrances, Inc.
[15]available from International Flavors and Fragrances, Inc.

Examples of Perfume Blends of Odor Masking Base and Perfume Oil

|  | w/w ratio |
|---|---|
| Perfume Blend A | |
| Odor Masking Base: Example VIII | 50 |
| Perfume Oil | 50 |
| Perfume Blend B | |
| Odor Masking Base: Example VII | 30 |
| Perfume Oil | 70 |
| Perfume Blend C | |
| Odor Masking Base: Example III | 20 |
| Perfume Oil | 80 |
| Perfume Blend D | |
| Odor Masking Base: Example II | 10 |
| Perfume Oil | 90 |

Styling Shampoo Compositions

| Component | IX WT % | X WT % | XI WT % | XII WT % | XIII WT % |
|---|---|---|---|---|---|
| Ammonium Laureth Sulfate | 10.5 | 9.5 | 10.0 | 2.0 | 14.0 |
| Ammonium Lauryl Sulfate | 0.5 | — | — | — | — |
| Lauroamphoacetate | 7.0 | — | — | — | — |
| Cocamidopropyl Betaine FB | — | 4.3 | 4.0 | 6.0 | 2.7 |
| Mixture A | 4.0 | — | — | — | — |
| Mixture B | — | 8.0 | — | — | — |
| Mixture C | — | — | 12.0 | — | — |
| Mixture D | — | — | — | 3.0 | 6.0 |
| Monosodium Phosphate | 0.1 | 0.1 | 0.1 | 0.1 | 0.1 |
| Disodium Phosphate | 0.2 | 0.2 | 0.2 | 0.2 | 0.2 |
| Glycol Distearate | 2.0 | 2.0 | 2.0 | 2.0 | 2.0 |
| Cocomonoethanol amide | 0.6 | 0.6 | 0.6 | 0.6 | 0.6 |
| Perfume Blend A | — | — | 1.0 | — | — |
| Perfume Blend B | — | 1.0 | — | — | — |
| Perfume Blend C | 1.0 | — | — | — | 1.0 |
| Perfume Blend D | — | — | — | 1.0 | — |
| Cetyl Alcohol | 0.42 | 0.42 | — | 0.42 | 0.60 |
| Stearyl Alcohol | 0.18 | 0.18 | 0.18 | 0.18 | — |
| PEG-150 Pentaerythrityl Tetrastearate | 0.2 | 0.5 | 0.7 | 0.9 | 1.0 |
| Polyquaternium 10 (JR30M) | — | 0.3 | 0.5 | 0.15 | — |
| Polyquaternium 10 (JR400) | 0.3 | — | — | — | 0.5 |
| Dimethicone | — | 0.3 | 0.3 | — | — |
| DMDM Hydantoin | 0.2 | 0.2 | 0.2 | 0.2 | 0.2 |
| Water | qs 100 | qs 100 | qs 100 | qs 100 | qs 100 |

Styling Shampoo Compositions -continued

| Component | w/w ratio |
|---|---|
| Mixture A. | |
| Styling Polymer: t-butyl acrylate/2-ethylhexyl methacrylate (90/10 w/w) | 40 |
| Liquid carrier: isododecane | 60 |
| Mixture B. | |
| Styling Polymer: vinyl pyrrolidone/vinyl acetate (5/95 w/w) | 50 |
| Liquid carrier: amyl benzoate | 50 |
| Mixture C. | |
| Styling Polymer: vinyl pyrrolidone/vinyl acetate (5/95 w/w) | 50 |
| Liquid carrier: benzyl alcohol | 50 |
| Mixture D. | |
| Styling Polymer: vinyl pyrolidone/vinyl acetate (5/95 w/w) | 40 |
| Liquid carrier: diethyl succinate | 60 |

| Component | XIV WT % | XV WT % | XVI WT % | XVII WT % | XVIII WT % |
|---|---|---|---|---|---|
| Ammonium Laureth Sulfate | 9.5 | 9.0 | 9.3 | 9.3 | 9.5 |
| Ammonium Lauryl Sulfate | 1.0 | 3.0 | — | — | 1.0 |
| Lauroamphoacetate | 7.5 | 6.0 | — | — | 7.5 |
| Cocamidopropyl Betaine FB[1] | — | — | 4.7 | 4.7 | — |
| Polyquaternium-16 (Luviquat FC 370)[2] | 2.0 | 3.0 | 3.0 | 1.5 | 2.5 |
| Monosodium Phosphate | 0.1 | 0.1 | 0.1 | 0.1 | 0.1 |
| Disodium Phosphate | 0.2 | 0.2 | 0.2 | 0.2 | 0.2 |
| Glycol Distearate | 2.0 | 2.0 | 2.0 | 2.0 | 2.0 |
| Cocomonoethanol amide | 0.6 | 0.6 | 0.6 | 0.6 | 0.6 |
| Perfume Blend A | — | — | 1.0 | — | 1.0 |
| Perfume Blend B | — | 1.0 | — | — | — |
| Perfume Blend C | 1.0 | — | 1.0 | — | — |
| Perfume Blend D | — | — | — | 1.0 | — |
| Cetyl Alcohol | 0.07 | — | 0.42 | 0.42 | 0.14 |
| Stearyl Alcohol | 0.03 | — | 0.18 | 0.18 | 0.06 |
| PEG-150 Pentaerythrityl Tetrastearate | 0.1 | 0.15 | — | 0.08 | 0.20 |
| Polyquaternium 10 (JR30M)[3] | 0.3 | — | 0.3 | — | 0.2 |
| Polyquaternium 10 (JR400)[3] | — | — | — | 0.4 | — |
| Guar Hydroxypropyltrimonium Chloride (Jaguar C-17)[4] | — | 0.3 | — | — | — |
| Dimethicone | 0.25 | — | — | — | — |
| DMDM Hydantoin | 0.2 | 0.2 | 0.2 | 0.2 | 0.2 |
| Water | qs 100 | qs 100 | qs 100 | qs 100 | qs 100 |

[1]Available from Goldschmidt (Hopewell, Virginia, USA)
[2]Available from BASF (Ludwigshafen, Germany)
[3]Available from Amerchol Corp. (Edison, NJ, USA)
[4]Available from Rhone-Poulene (Cranbury NJ, USA)

After Shave/Cologne Compositions

| Component | XIX WT % | XX WT % | XXI WT % | XXII WT % |
|---|---|---|---|---|
| Ethanol | 61.55 | 79.30 | 74.30 | 60.00 |
| Isoprdpanol | — | — | 5.00 | 10.00 |
| Benzophenone | 0.10 | 0.10 | 0.10 | 0.10 |
| Dimethicone[1] | 0.2 | 0.2 | 0.2 | 0.2 |
| Perfume Blend A | 1.0 | — | — | — |
| Perfume Blend B | — | — | 1.0 | — |
| Perfume Blend C | — | 1.0 | — | — |
| Perfume Blend D | — | — | — | 1.0 |
| Dipropylene Glycol | 0.0053 | 0.011 | 0.053 | 0.0265 |
| Water | qs 100 | qs 100 | qs 100 | qs 100 |

[1]Dow Corning 200 Fluid - 20 cs

What is claimed is:

1. A method of masking the malodor of a malodor-producing polymer in personal care compositions, said method comprising the steps of:

(a) preparing an odor masking base by combining the following components:
    (i) from about 20% to about 80% by weight of the base of a highly volatile perfume having a boiling point of less than about 250° C.,
    (ii) from about 15% to about 75% by weight of the base of an ione perfume having a boiling point of more than about 25° C., and
    (iii) from about 5% to about 65% by weight of the base of a musk having a boiling point of more than about 250° C.; and
  (b) mixing the odor masking base of step (a) with a malodor-producing polymer selected from the group consisting of crosslinked nonionic polyacrylate polymers, crosslinked cationic Polyacrylate polymers, polysaccharides, crosslinked acrylic acid copolymers, copolymers of alkyl vinyl ether and maleic anhydride, polyvinyl (N-pyrrolidones), polydimethylsiloxane gums, silicone elastomers, siloxane gums, resin reinforced siloxanes, crosslinked siloxane polymers, silicone copolymers, and mixtures thereof;

17 wherein the composition comprises from about 0.005% to about 2.5% by weight of the odor masking base, and from about 0.1% to about 99.85% by weight of the malodor-producing polymer.

2. The method of claim 1 wherein the composition comprises from about 0.5% to about 50% by weight of the malodor-producing polymer.

3. The method of claim 1 wherein the composition comprises from about 0.006% to about 1% by weight of the odor masking base.

4. The method of claim 3 wherein the odor masking base comprises from about 16% to about 40% by weight of the ionone perfume, from about 15% to about 50% by weight of the musk, and from about 35% to about 75% by weight of the highly volatile perfume.

5. The method of claim 4 wherein the ionone perfume is selected from a group consisting of methyl ionones; alpha ionones, beta ionones, gamma ionones, and mixtures thereof.

6. The method of claim 4 wherein the musk is selected from the group consisting of polycyclic musks, macrocyclic musks, nitrocyclic musks, and mixtures thereof.

7. The method of claim 4 wherein the highly volatile perfume is selected from the group consisting of aldehydes having from 2 to 15 carbon atoms, esters having from 3 to 15 carbon atoms, alcohols having from 4 to 12 carbon atoms, ethers having from 4 to 13 carbon atoms, ketones having from 3 to 12 carbon atoms, and mixtures thereof.

8. The method of claim 7 wherein the aldehyde is selected from the group consisting of n-decyl aldehyde, 10-undecen-1-al, dodecanal, 3,7-dimethyl-7-hydroxyoctan-1-al, 2,4-dimethyl-3-cyclohexene carboxaldehyde, benzaldehyde, and mixtures thereof.

9. The method of claim 7 wherein the ester is selected from the group consisting of ethyl acetate, cis-3-hexenyl acetate, 2,6-dimethyl-2,6-octadien-8-yl acetate, benzyl acetate, 1,1-dimethyl-2-phenyl acetate, 2-pentyloxy allyl ester, and mixtures thereof.

10. The method of claim 7 wherein the alcohol is selected from the group consisting of n-octyl alcohol, beta gamma-hexenol, 2-trans-6cis-nonadien-1-ol, 3,7-dimethyl-trans-2, 6-octadien-1-ol, 3,7-dimethyl-6-octen-1-ol, 2,6-dimethyl-7-octen-2-ol, 2-phenylethyl alcohol, and mixtures thereof.

11. The method of claim 7 wherein the ketone is selected from the group consisting of dimethyl acetophenone, ethyl-n-amyl ketone, 2-heptanone, 2-octanone, 3-methyl-2-(cis-2-penten-1-yl)-2-cyclopenten-1-one, 1,1-methyl-4-isopropenyl-6-cyclohexen-2-one, para-tertiary-amyl cyclohexanone, and mixtures thereof.

12. The method of claim 1 wherein the composition further comprises from about 0.05% to about 5% by weight of a perfume oil, and has a weight ration of perfume oil to odor masking base of from about 50:50 to about 95:5.

13. A method of the malodor of a malodor-producing liquid carrier in personal care compositions, said method comprising the steps of:
(a) preparing an odor masking base by combining the following components:
(i) from about 20% to about 80% by weight of the base of a highly volatile perfume having a boiling point of less than about 250° C.,
(ii) from about 15% to about 75% by weight of the base of an ionone perfume having a boiling point of more than about 250° C., and
(iii) from about 5% to about 65% by weight of the base of a musk having a boiling point of more than about 250° C.; and

18

(b) mixing the odor masking base of step (a) with a malodor-producing liquid carrier wherein the malodor-producing liquid carrier is a volatile solvent selected from the group consisting of hydrocarbons having from 8 to 18 carbon atoms, isoamyl ether, dipentyl ether, dihexyl ether, $C_5$–$C_{12}$ alkyl esters $C_1$–$C_4$ alcohols, aryl alcohol, benzyl alcohol, phenyl propanol, volatile cyclic polydialkylsiloxane, volatile linear polydialkylsiloxane, silane compounds, and mixtures thereof;

wherein the composition comprises from about 0.005% to about 2.5% by weight of the odor masking base, and from about 0 1% to about 99.85% by weight of the malodor-producing liquid carrier.

14. The method of claim 13 wherein the composition comprises from about 1% to about 50% by weight of the volatile solvent.

15. The method of claim 13 wherein the composition comprises from about 0.006% to about 1% by weight of the odor masking base.

16. The method of claim 15 wherein the odor masking base comprises from about 16% to about 40% by weight of the ionone perfume, from about 15% to about 50% by weight of the musk, and from about 35% to about 75% by weight of the highly volatile perfume.

17. The method of claim 16 wherein the ionone perfume is selected from the group consisting of methyl ionones, alpha ionones, beta ionones, gamma ionones, and mixtures thereof.

18. The method of claim 16 wherein the musk is selected from the group consisting of polycyclic musks, macrocyclic musks, nitrocyclic musks, and mixtures thereof.

19. The method of claim 16 wherein the highly volatile perfume is selected from the group consisting of aldehydes having from 2 to 15 carbon atoms, esters having from 3 to 15 carbon atoms, alcohols having from 4 to 12 carbon atoms, ethers having from 4 to 13 carbon atoms, ketones having from 3 to 12 carbon atoms, and mixtures thereof.

20. The method of claim 19 wherein the aldehyde is selected from the group consisting of n-decyl aldehyde, 10-undecen-1-al, dodecanal, 3,7-dimethyl-7-hydroxyoctan-1-al, 2,4-dimethyl-3-cyclohexene carboxaldehyde, benzaldehyde, and mixtures thereof.

21. The method of claim 19 wherein the ester is selected from the group consisting of ethyl acetate, cis-3-hexenyl acetate, 2,6-dimethyl-2,6-octadien-8-yl acetate, benzyl acetate, 1,1-dimethyl-2-phenyl acetate, 2-pentyloxy allyl ester, and mixtures thereof.

22. The method of claim 19 wherein the alcohol is selected from the group consisting of n-octyl alcohol, beta-gamma-hexenol, 2-trans-6-cis-nonadien-1-ol, 3,7-dimethyl-trans-2,6-octadien-1-ol, 3,7-dimethyl-6-octen-1-ol, 2,6-dimethyl-7-octen-2-ol, 2-phenylethyl alcohol, and mixtures thereof.

23. The method of claim 19 wherein the ketone is selected from the group consisting of dimethyl acetophenone, ethyl-n-amyl ketone, 2-heptanone, 2-octanone, 3-methyl-2-(cis-2-penten-1-yl)-2-cyclopenten-1-one, 1,1-methyl-4-isopropenyl-6-cyclohexen-2-one, para-tertiary-amyl cyclohexanone, and mixtures thereof.

24. The method of claim 13 wherein the composition further comprises from about 0.05% to about 5% by weight of a perfume oil, and has a weight ratio of perfume oil to odor masking base of from about 50:50 to about 95:5.

* * * * *